(12) United States Patent
Avrameas et al.

(10) Patent No.: US 6,608,034 B1
(45) Date of Patent: Aug. 19, 2003

(54) IMMUNOVECTORS FOR THE INTRACELLULAR AND INTRANUCLEAR TRANSPORT

(75) Inventors: Stratis Avrameas, Paris (FR); Gerard Buttin, Paris (FR); Therese Ternynck, Paris (FR); Faridabano Nato, Antony (FR); Alexandre Avrameas, Vitry sur Seine (FR)

(73) Assignees: Institut Pasteur, Paris (FR); Universite Pierre et Marie Curie (Paris VI), Paris (FR)

( * ) Notice: Subject to any disclaimer, the term of this patent is extended or adjusted under 35 U.S.C. 154(b) by 0 days.

(21) Appl. No.: 08/981,474

(22) PCT Filed: Jul. 10, 1996

(86) PCT No.: PCT/FR96/01076

§ 371 (c)(1),
(2), (4) Date: Apr. 28, 1998

(87) PCT Pub. No.: WO97/02840

PCT Pub. Date: Jan. 30, 1997

(30) Foreign Application Priority Data

Jul. 10, 1995 (FR) .............................. 95 08316

(51) Int. Cl.[7] ........................ A61K 31/70; C07H 21/02; C07H 16/00; C07H 17/00
(52) U.S. Cl. ..................... 514/44; 536/23.1; 530/388.1; 530/388.21; 530/391.1
(58) Field of Search ........................ 514/44; 424/93.21, 424/130.1, 133.1, 136.1, 178.1, 188.1; 435/69.1, 325, 455; 530/388.1, 388.21, 391.1, 391.7; 536/23.1

(56) References Cited

U.S. PATENT DOCUMENTS 4,812,397 A * 3/1989 Weisbart et al. ................ 435/7
5,908,777 A * 6/1999 Lee et al. ................. 435/320.1
5,922,859 A   7/1999 Birnstiel et al.

OTHER PUBLICATIONS

Anderson, "Human gene therapy", Nature, 392(Supp.):25–30, Apr. 1998.*
Verma et al., "Gene theray–promises, problems and prospects", Nature, 389:239–242, Sep. 1997.*
Zabner, "Cationic lipids uses in gene transfer", Adv. Drug Deliv. Rev., 27:17–28, 1997.*
Chu et al., "Binding and uptake of cationic lipid:pDNA complexes by polarized airway epithelial cells", Hum. Gene Ther., 10:25–36, Jan. 1999.*
Zabner et al., "Cellular and molecular barriers to gene transfer by a cationic lipid", J. Biol. Chem., 270(32):18897–19007, Aug. 1995.*
Feldherr, "Macromolecular exchanges between th nucleus and cytoplasm", J. Cell. Biochem Suppl., 30/31:214–219, 1998.*
Sebestyen et al., "DNA vector chemistry: the covalent attacement fo signal peptides to plasmid DNA", Nature Biotech., 16:80–85, Jan. 1998.*
Ludtke et al., "A nuclear localization signal can enhance both the nuclear transport and expression of 1 kb DNA", J. Cell Sci., 112(Pt 12):2033–2041, Jun. 1999.*
Lucas et al., Pharmaceutical and biological properties of poly(amino acid)/DNA polyplexes, J. Drug Target., 7(2):143–156, 1999.*
Whitttaker et al., "Nuclear import and export of viruses and virus genomes", Virol., 246:1–23, Jun. 1998.*
Lechardeur et al., "Metabolic instability of plasmid DNA in the cytosol: a potential barrier to gene transfer", Gene Ther., 6:482–497, Apr. 1999.*
Vlahakos et al., "Murine monoclonal anti–DNA antibodies penetrate cells, bind to nuclei, and induce glomerular proliferation and proteinuria in vivo", J. Am. Soc. Nephr., 2(8):1345–1354, Feb. 1992.*
Fominaya et al., "Target cell–specific DNA transfer mediated by a chimeric multidomain protein", 271(18):10560–10568, May 1996.*
Yanase et al., "A subgroup of murine monoclonal anti–deoxyribonucleic acid antibodies traverse the cytoplasm and enter the nucleus in a time and temperature–dependent manner", Lab. Invest., 71(1):52–60, Jul. 1994.*
Anderson, "Human gene therapy", Nature, 392(Supp.):25–30, Apr. 1998.*
Verma and Somia, "Gene therapy–promises, problems and prospects", Nature, 389:239–242, Sep. 1997.*
Madaio et al. "Cellular penetration and nuclear localization . . . " J Autoimm. 11:535–538 (1998).*

* cited by examiner

*Primary Examiner*—Deborah Crouch
*Assistant Examiner*—Joseph Woitach
(74) *Attorney, Agent, or Firm*—Oblon, Spivak, McClelland, Maier & Neustadt, P.C.

(57) ABSTRACT

A product for coupling a biologically active principle with an immunovector, characterized in that the immunovector is capable of enabling the biologically active principle to be internalized into eukaryotic cells, and in that said immunovector has an affinity for the cell DNA to such an extent that it can transfer the biologically active principle into or to the immediate vicinity of the cell nuclei.

17 Claims, 6 Drawing Sheets

IMMUNOVECTORS FOR THE INTRACELLULAR AND INTRANUCLEAR TRANSPORT

CROSS-REFERENCE TO RELATED APPLICATIONS

Figure 1A:
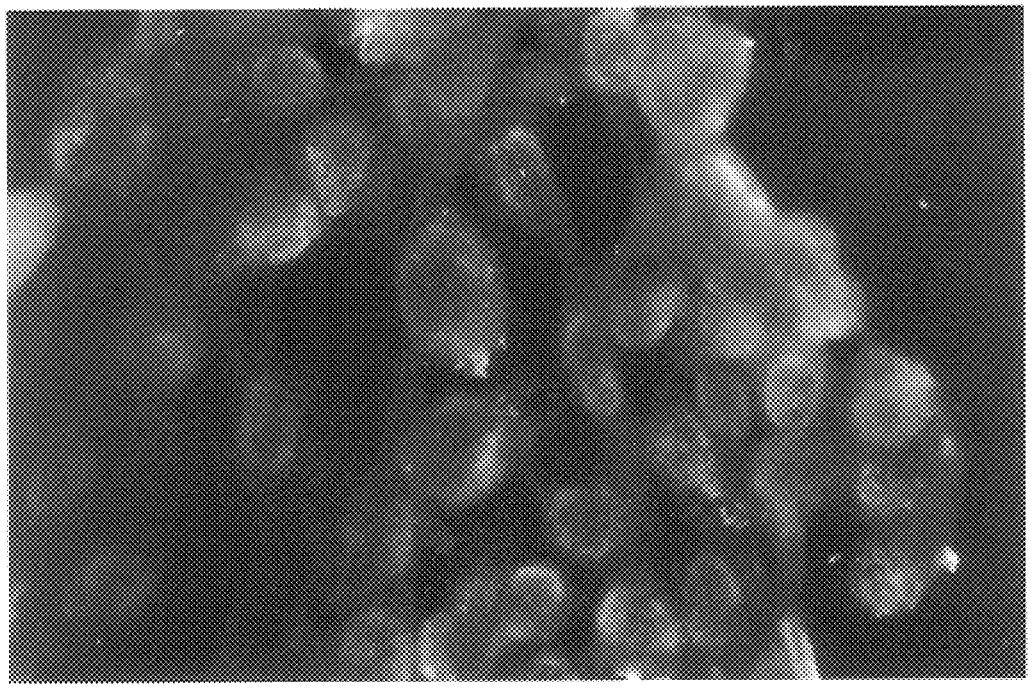
Figure 1B:
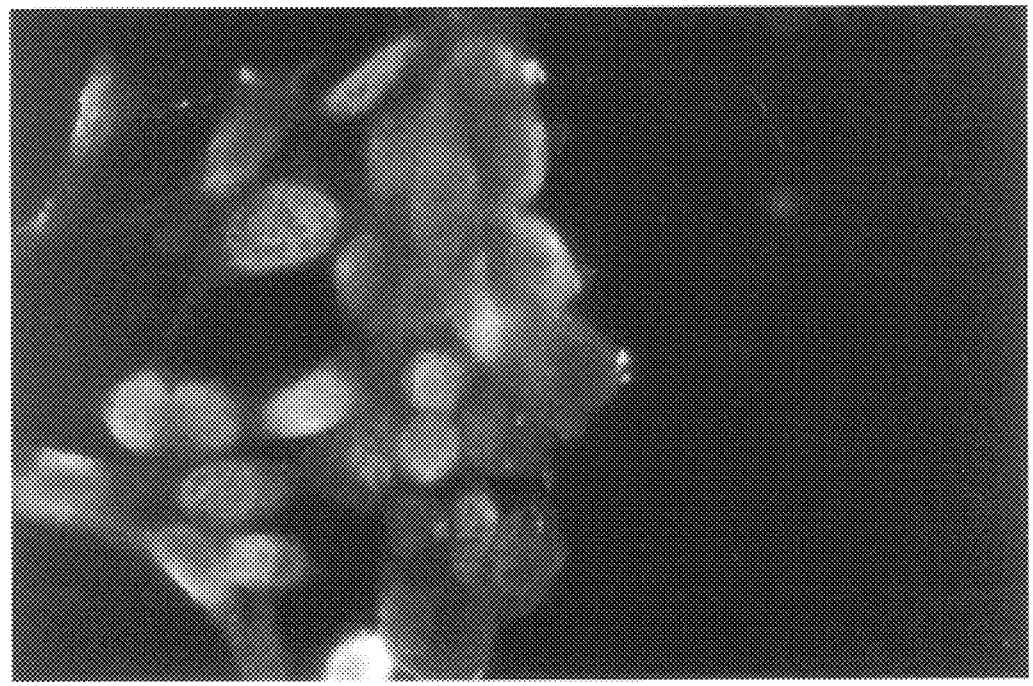
Figure 1C:
Figure 1D:
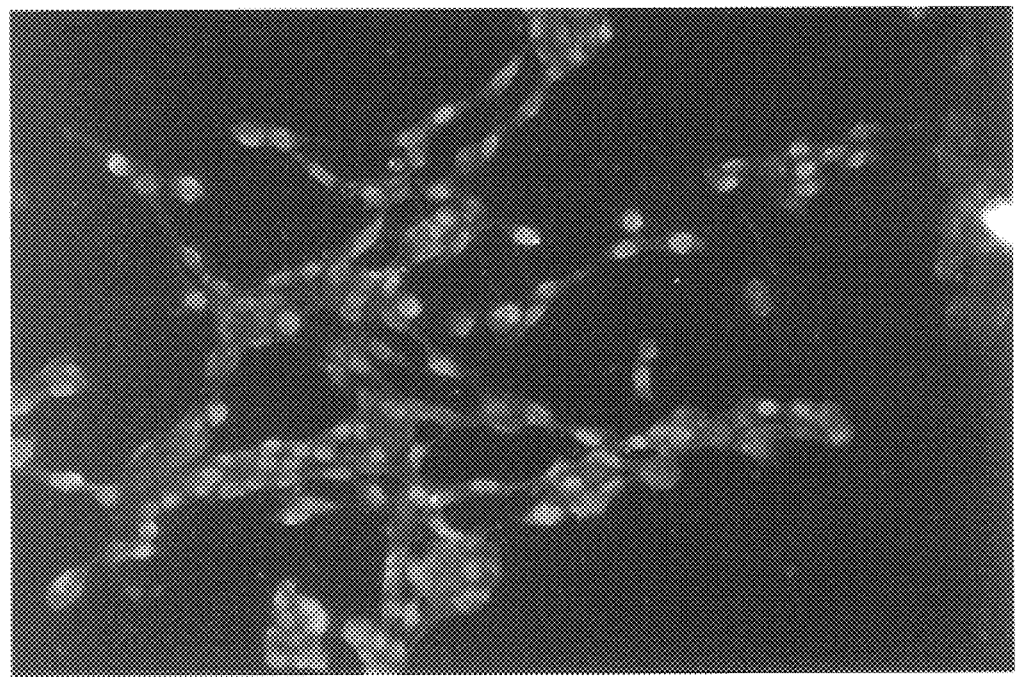

This application claims priority under 35 U.S.C. §3712 PCT/FR 96/01076 filed Jul. 10, 1996 which is incorporated herein by reference.

BACKGROUND OF THE INVENTION

Field of the Invention

The present invention relates to the active transfer of haptens, proteins, nucleic acids and other molecules into the nucleus of eucaryotic cells. This invention is of major importance since it can be applied to various fields, especially those of gene therapy and vaccines.

Gene therapy continues to be dependent on a considerable number of parameters among which are the development of vectors capable of transporting through the cytoplasm of these cells of the host organism active principles endowed with predetermined specific properties into the nuclei of cells of the organism in the absence of genetic alterations associated with the use of these vectors, and the non-degradation of the biological activity of the active principles transferred. It is known that so far all these conditions are far from being fulfilled (1).

Indeed, the current methods commonly used to transfer DNA into cells are the following: general, non-selective methods which use the property of DNA to coprecipitate with calcium phosphate or DEAE-dextran, or alternatively the direct introduction of DNA into cells under the effect of an electric field (electroporation). These methods are very toxic for the cells, leading to a high mortality and a high variability according to the cells used. Other methods use targeting of the entry of the gene into cells by receptors present on their membrane. The DNA may then penetrate into the cell via either a ligand specific for these receptors: asialorosomucoid (2), insulin (3) or transferrin (4), or antibodies specific for membrane constituents (5). The DNA/ligand complex penetrates into the cell by a process of endocytosis. The transfection is therefore limited by a substantial destruction of the complex in the lysosomal vesicles, and different methods have been proposed to overcome these disadvantages, especially the blocking of the lysosomal compartment by chloroquine or the simultaneous addition of adenoviruses which escape the endosomal compartment by destroying the membrane of the endocytosis vesicles (6).

The aim of the present invention is to provide a new type of vectors which are both more efficient and safer than the viral vectors whose use has been envisaged until now.

The invention therefore relates to a product of coupling between a biologically active principle and one of these new vectors, hereinafter called "immunovectors", the said product of coupling being characterized both by the capacity of the immunovector to allow the internalization in eucaryotic cells of biologically active principles linked covalently or non-covalently to these immunovectors, and by their affinity for the DNA of these cells to such a point that the said immunovector is rendered capable of transferring the biologically active principle immediately close to the nuclei of these cells or into the nuclei of these cells.

These immunovectors preferably consist of antibodies or fragments of antibodies capable of recognizing DNA sequences inside these cells, and to which biologically active principles may be covalently or non-covalently linked, these antibodies or fragments of antibodies being, in addition, capable of transporting in vitro and in vivo these biologically active principles through the membranes and the cytoplasm of these cells, and transferring them close to or even into the nucleus of these cells.

It is understood that in the present description the term "biologically active principle" relates to any molecule, macromolecule or group of molecules having biological activity of the type in question.

The invention also relates to a method of transferring especially haptens, proteins and/or nucleic acids into the nucleus of cells, particularly eucaryotic cells, this method being based on the use of the properties of the said immunovectors.

The existence of antibodies capable of penetrating inside the nuclei of human lymphocytes when these cells are incubated in vitro in a culture medium containing a serum obtained from patients suffering from disseminated erythematous lupus (DLE) was reported for the first time by Alarcon-Segovia et al. in 1978 (7). Subsequently, the same team demonstrated that these antibodies are of the IgG isotype and are capable of reacting with ribonucleic acids, free or complexed with proteins (8). Recently, this type of antibody was detected in MRL lpr/lpr lupus mice, but also in NZB mice having a haemolytic auto-immune disease syndrome and even in normal BALB/c mice. Some monoclonal antibodies, prepared from the spleen of these mice, have proved capable of penetrating in vitro into the nucleus of cells maintained in culture (10–13). As in humans, it was noted that these monoclonal antibodies were capable of recognizing nucleic acids. Furthermore, it was shown that these antibodies are also capable, when they are injected into mice, of penetrating into several types of cells, ending up in their nuclei (11).

The invention results from the discovery that this type of antibody or fragments of these antibodies could also be used as vectors, hereinafter "immunovectors" capable of transporting biologically active principles, such as haptens, proteins, and nucleic acids through the membranes and the cytoplasm of the corresponding cells, and ensuring their transfer into the nucleus of the said cells.

These antibodies may be obtained in polyclonal form from a serum, in particular from an animal previously immunized against nucleic acid fragments having the corresponding epitope, or in monoclonal form from hybridomas secreting such antibodies.

Any type of bonding, chemical or otherwise, may be used to ensure the coupling of an immunovector of antibody or antibody fragment type having an affinity for the nucleic acids to the biologically active principle, for example a hapten or a nucleic acid, for the purpose of transporting it through the membranes and the cytoplasm of the cells, and to ensure the transfer of these active principles into the nucleus.

Preferably, a chemical mode of coupling, allowing the formation of covalent or non-covalent bonds, will be used.

Preferred coupling products are those in which the immunovectors are selectable by a cellular penetration test comprising a first incubation of the immunovector of interest in the presence of cells in culture in the nucleus of which the active principle capable of being associated with the immunovector has to be transported, followed, after fixing and permeabilization of these cells, by another incubation with labelled anti-immunovector antibodies, and finally by a detection immediately close to the nucleus or even inside the nucleus of the antigen-antibody type immunologic reaction between the immunovector and the anti-immunovector antibody.

Among the preferred immunovectors of the present invention, there may be mentioned the antibodies having an affinity for a nucleic acid, or a fragment thereof, the latter retaining this affinity.

Antibodies also having the capacity to bind to the cells, in particular lymphoid cells, can also be used. The latter category of immunovectors may also be selected by a test, which may then also comprise the incubation of the immunovectors of interest with lymphoid cells, washing the said lymphoid cells, incubating them with labelled anti-immunovector antibodies, and determining the number of positive cells in each population.

In one embodiment, the lymphoid cells used are auto-immune mouse splenocytes exhibiting a lupus syndrome.

A preferred immunovector for the coupling product is chosen from among monoclonal IgG's, (Fab')2 or (Fab') fragments, or any polypeptide corresponding to the site(s) of the antibodies involved in the recognition of the corresponding nucleic acid.

Preferably, this immunovector is an immunoglobulin, more particularly an IgG carrying an anti-DNA activity, and obtained from normal individuals.

In addition, this immunovector may be an IgG carrying an anti-DNA activity and obtained from individuals presenting auto-immune syndromes, more particularly disseminated erythematous lupus syndromes.

In a specific embodiment of the invention, the immunovector coupled to the active principle is a bi-specific antibody recognizing on the one hand the DNA, and on the other hand a protein such as Tat, Rev of the HIV retrovirus, as well as surface markers such as CD3, CD4, CD8, CD19 and CD34.

Preferably, the biologically active principle coupled to the immunovector is a molecule selected from especially nucleic acids, proteins especially enzymes, for example peroxidase, haptens especially biotin or fluorescein, enzyme activators or inhibitors and medicaments.

In a preferred embodiment, the coupled nucleic acid is a polynucleotide, the immunovector being an IgG, with the coupling being carried out via p-benzoquinone at the rate of one molecule of immunovector per 4 molecules of polynucleotide.

A biologically active principle preferably used consists of a plasmid intended to integrate into the nucleus of the target cells for the expression of a protein encoded by a gene contained in the said plasmid. When such a plasmid is coupled to an immunovector of the antibody type, having affinity for DNA, this immunovector is, preferably, previously coupled to an agent capable of inducing a compacting effect on the DNA, this agent being preferably polylysine.

Indeed, polylysine, which by virtue of its cationic properties is capable of compacting DNA, promotes the transfection of cells. The coupling of polylysine to the immunovector, which is carried out with the aid of a coupling agent, more particularly a carbodiimide such as EDC (1-(3-dimethylaminopropyl)-1'-ethylcarbodiimide), allows the DNA to react therewith. This has the effect of inducing the liberation of the active site of the antibody which may sometimes be masked when the antibody is coupled to an active principle of the size of a plasmid.

Other agents capable of having, by virtue of their cationic properties, a compacting effect on DNA (2–6) may also be coupled to the immunovector to fulfil such a function.

More specifically, a biologically active principle preferably used consists of a gene intended to integrate in the genome of target cells, especially by homologous recombination, more particularly a "nude" DNA containing a nucleic acid sequence coding for a polypeptide originating from bacterial or eucaryotic cells, fungal cells or viruses, this polypeptide having vaccinating properties.

Advantageously, this active principle allows the immortalization of selected types of cells, particularly macrophages, dendritic cells, B and T cells, and hematopoietic cells, especially of human origin.

Still more preferably, this biologically active principle is an antisense oligonucleotide allowing the inhibition of protein or nucleotide synthesis, for example in cells infectable by an HIV retrovirus, or in tumour cells.

Thus, the inventors have, on the one hand, tried to obtain, from the spleen of autoimmune mice (NZB×NZW)F1, having a lupus syndrome, IgG monoclonal antibodies which have been selected for their capacity to react with DNA but also for their capacity to penetrate as far as the nucleus of the cells. In parallel, polyclonal antibodies reacting with the DNA and capable of penetrating into the nuclei of the cells have been isolated by affinity chromatography. This chromatography was applied either to a "pool" of sera of normal patients or to a normal individual serum, preferably to sera obtained from patients suffering from infections, particularly to a serum of normal patients suffering from DLE, or to a mouse (NZB×NZW)F1 serum.

In a method of selection of immunovectors according to the present invention, the test of cellular penetration of the immunovectors comprises a first incubation of eucaryotic cell lines in a medium comprising the said immunovectors preferably in increasing concentration, then the fixing, and, if necessary, the permeabilization, or vice versa, of these cells, followed by an incubation of the said cell lines with anti-immunovector antibodies preferably labelled with fluorescein or with peroxidase, and the localization of the antibodies thus labelled close to the nuclei of the said cells or better still inside the nuclei. The cell lines are especially chosen from among fibroblasts, thymocytes or splenocytes.

Without the following reaction conditions having a limiting character, it may be mentioned that the first incubation is often carried out at 37° C., for about 2 to 8 hours with immunovector concentrations of about 1 to 70 $\mu$g/ml, on cell lines inoculated at a concentration ranging from $5 \times 10^3$ to $5 \times 10^6$ cells per milliliter.

In one of the embodiments of the method, the cell line is a fibroblast line in exponential growth inoculated at a concentration of $2 \times 10^4$ cells per milliliter, or thymocytes or splenocytes of BALB/c mice, which are suspended at the rate of about $10^6$ cells per milliter.

Moreover, the invention relates to a method of preparation of immunovector-molecule(s) coupling product, the immunovectors being chosen from among antibodies, more particularly the IgG's obtained according to the method of selection, (Fab')2 or (Fab') fragments, or any polypeptide corresponding to the site of the antibodies or fragments of antibodies involved in the transport of the molecules.

In the method of preparation of a coupling product according to the invention, it is ensured that for each immunovector is coupled at least one molecule of biologically active product, the said molecule being preferably covalently linked to the immunovector.

The following examples illustrate conditions in which haptens such as fluorescein and biotin, small molecules such as hormones, proteins preferably enzymes, enzyme inhibitors or activators and medicines, for example antivirals such as acyclovir or AZT, may be actively transported through the cytoplasm of the treated cells and transferred into the nucleus of the said cells. In particular, fluorescein has been coupled to the free amino groups of the immunovectors via an active isothiocyanate group and the biotin via an active succinimide ester. The coupling of the haptens and the like to the immunovector may be carried out by means of other homo- or heterobifunctional bridging groups or reagents known in the literature, such as the imido esters and N-hydroxysuccinimidyl esters which are capable of reacting with the amino groups, for example derivatives of alkyl, haloaryl, haloacetyl and pyridyl disulphide groups reacting preferentially, maleimides, or by means of sulphydryl groups, carbodiimides, as well as molecules having photo-activable groups such as azidobenzoyl hydrazide (13).

In addition, the inventors have prepared products of coupling where the immunovector is a bi-specific antibody against a target antigen, constructed either by the chemical route or by the genetic engineering route, and have in parallel immunized individuals, for example mice, with the said target antigens, and selected immunovectors which are bi-specific antibodies preferably reacting with the said target antigens, such that the action of the immunovectors is directed specifically.

Techniques relating to the synthesis of bi-specific antibodies have especially been described by Porstmann et al. in 1984 (16), a study entitled "Development of a bispecific monoclonal antibody for use in molecular hybridisation" having moreover been published in 1984 by Auriol et al. (17).

Advantageously, the bi-specific antibodies used in this method recognize, inter alia, the proteins Tat, Rev of the HIV retrovirus, as well as surface markers CD3, CD4, CD8, CD19 and CD34.

Moreover, the present invention relates to a method for transferring an active principle in the nuclei of selected eucaryotic cells, characterized by coupling this active principle with an immunovector having both the capacity of allowing internalization of this active principle in these eucaryotic cells and an affinity for the DNA of these cells to such a point that the said immunovector is rendered capable of transporting this biologically active principle immediately close to or into the nuclei of these cells.

This biologically active principle may be covalently or non-covalently coupled to the immunovector.

Preferably, this method of transfer is characterized in that the immunovector entering into the composition of this product is selected from those which are selectable by a cellular penetration test comprising a first incubation of the immunovector of interest in the presence of cells in the nucleus of which the active principle capable of being associated with the immunovector has to be transported, followed, after fixing and permeabilization of these cells, by another incubation with labelled anti-immunovector antibodies, and finally the detection immediately close to the nucleus or even in the nucleus of the antigen-antibody type immunologic reaction between the immunovector and the anti-immunovector antibody.

In a preferred embodiment of the method of transfer according to the invention, the immunovector used is formed of an antibody having an affinity for a nucleic acid, or of a fragment of this antibody retaining this affinity.

This immunovector used in this method is preferably selected from among antibodies, preferably monoclonal IgG's, (Fab')2 or (Fab') fragments, or any polypeptide corresponding to the site(s) of the antibodies involved in the recognition of the corresponding nucleic acid.

Advantageously, once the product of immunovector/active principle coupling is prepared, it may be used for the intranuclear transfer of other molecules. Thus, the fluorescein/immunovector conjugate tested may be associated with an anti-fluorescein antibody coupled with a third molecule, and thus transfer the said third molecule into the nuclei of the cells. Similarly, the biotin/immunovector conjugate may allow the binding of an anti-biotin antibody or of avidin-streptavidin coupled with a third molecule to be transferred into the nuclei.

In the present invention, an enzyme such as horseradish peroxidase was transferred into the nucleus, but other proteins having varied biological activities may also be used. Peroxidase coupled to the immunovector via glutaraldehyde has also been used. However, other methods known in the literature, such as those described in the case of haptens, may also be used.

As in the case of the hapten/immunovector conjugates, there may be used, in association with the protein/immunovector conjugates, an anti-protein antibody coupled with a third molecule for the intranuclear transfer of the said molecule.

In the invention described herein, although a polynucleotide has been transferred into the nucleus, a wide variety of nucleic acids having appropriate biological activities may also be actively transferred at the intranuclear level.

Thus, a method of transfer of active principles according to the invention allows in particular the transfer of genes intended to integrate into the genome of the target cells, especially by homologous recombination, more particularly the transfer of "nude" DNA, it being possible for the latter especially to be used as "DNA vaccine".

One of the homologous recombination techniques possible is that described by Mouellic et al. in 1990 (18).

Recent studies carried out by Whalen R. G. et al. have made it possible to show the existence of an immune response following a DNA transfer. These studies, which have been the subject of patent application WO 95/11307, were more particularly applied to the expression of monoclonal molecules of the IL2 cytokine type (19).

In addition, this method of transfer makes it possible to introduce nucleotide sequences involved in the immortalization of different cell types, particularly macrophages, dendritic cells, B and T cells, and haemotopoietic cells especially of human origin. As nucleotide sequences, there may be mentioned the oncogenic sequences or viral sequences associated with cell transformation phenomena.

It also allows the transfer of antisense oligonucleotides allowing the inhibition of protein or nucleotide synthesis, for example in cells infectible by a retrovirus such as HIV, or tumour cells.

In the present invention, the polynucleotide was coupled to the immunovector via p-benzoquinone. However, other methods known in the literature may also be used.

Moreover, the present invention also relates to the eucaryotic cells containing active molecules preferably at the nuclear level, characterized in that the said molecules cannot be naturally incorporated into the nuclei of the said cells or have a weak expression level in the said cells. These molecules are presented in these cells immediately close to their nuclei or into their nuclei, and are coupled to an immunovector characterized by its affinity for the DNA of these cells, in the form of a coupling product according to the invention.

Among the cells to which the present invention relates, there are especially the cells which can be infected by a virus or tumour cells.

Also entering within the framework of the present invention are the hybridomas producing the antibodies according to the present invention, as deposited at the CNCM on Jun. 30, 1995 under the numbers I-1605, I-1606 and I-1607.

In addition, the invention relates to a pharmaceutical composition, characterized in that it contains, in combination with a physiologically acceptable vehicle, a coupling product according to the invention in which the biologically active principle is a medicine or vaccinal active principle and the immunovector is compatible with the host organism to which the medicine is directed.

Also entering into the framework of the present invention is the use of the coupling product of the invention for the expression, in receiving cells, of a nucleotide sequence which is heterologous to the DNA of the host.

EXAMPLES

1. Preparation of Immunovectors

A) Polyclonal Immunovectors

The human or murine IgG's are first isolated by passage of a mixture of sera obtained from individuals suffering from disseminated erythematous lupus—or from lupus mice (NZB×NZW)F1—on protein A immobilized on Sepharose (14).

The isolated IgG's are passed over a column of DNA immobilized on cellulose. The specific anti-DNA antibodies present in these IgG's are attached to this DNA-cellulose immunoadsorbent and eluted with a 20 $\mu$M sodium carbonate-bicarbonate buffer, pH 10, containing 5% dimethyl sulphoxide (15). 1 to 2 mg of antibodies are thus isolated from 10 mg of IgG. The eluted antibodies are dialysed, concentrated and stored at +4° C. until they are used.

B) Murine Monoclonal Immunovectors

Splenocytes obtained from lupus mice (NZB×NZW)F1 are fused with the X63 myeloma according to the method of Köhler and Milstein. The hybridomas produced are tested by ELISA for the secretion of IgG and for their anti-DNA activity. The anti-DNA IgG secreting hybridomas are subcloned at least twice and the clones which remain doubly positive (IgG+anti-DNA) are bulk cultured or alternatively ascites are prepared from these clones in mice. In a typical experiment, starting with the spleen of a mouse (NZB× NZW)F1, approximately 300 positive wells secreting IgG's were obtained of which 60 were capable of reacting with DNA. After cloning, 20 clones secreted IgG recognizing DNA. Of these 20 clones, approximately half secreted antibodies capable of penetrating into the nucleus of the cells whereas the others were not capable of this (see C: test of intranuclear penetration of the immunovectors). The monoclonal IgG's are isolated from culture supernatants or ascitic fluids by precipitation with 45% ammonium sulphate followed, after dialysis, by passage on protein A immobilized on Sepharose. After neutralization of the eluted IgG's, the preparations are dialysed, concentrated and stored at −20° C. until they are used.

The mouse antibodies mentioned above will be subsequently humanized using one of known techniques, for example that described by Riechmann et al. (20).

C) Selection of the Immunovectors

1) Test of Intranuclear Penetration of the Immunovectors

Two fibroblast lines—PtK2 obtained from kangaroo rat kidney and GMA-32 obtained from hamster kidney—were mainly used. The slides carrying the fibroblasts in the exponential growth phase, inoculated at $2 \times 10^4$ cells/ml, 24 hours beforehand and cultured in RPMI 1640 or MEM medium (containing 10% foetal calf serum, 2 mM L-glutamine and 1% sodium pyruvate) are incubated at 37° C. in renewed culture medium, containing selected quantities of immunovector (1 to 70 $\mu$g/ml) After 2 to 4 hours of incubation, the cells are washed with PBS and fixed with either ethanol for 10 minutes at −20° C., or with 0.2% glutaraldehyde and 2% formaldehyde in PBS for 20 minutes. After three washes with PBS, the cells are permeabilized for 20 minutes in PBS containing 0.2% bovine serum albumin and 0.5% saponin.

The cellular preparations are then washed with PBS and incubated for 45 minutes at 24° C. with anti-mouse immunoglobulin (or anti-human immunoglobulin) rabbit or sheep antibodies labelled with fluorescein or with peroxidase (20 $\mu$g/ml). After washing, the cellular preparations incubated with the fluorescent antibody are examined under a fluorescence microscope. The cellular preparations incubated with the peroxidase-labelled antibody are first incubated in the cytochemical substrate of peroxidase (diaminobenzidine (DAB)+$H_2O_2$) and, after washing, the preparation is examined under an optical microscope (14). The number of positive cells is counted.

As described above, mouse thymocytes were also used to test the penetration of the immunovectors into the nucleus. Suspensions of thymocytes were prepared from BALB/c mouse thymus. The thymocytes, at a concentration of $1 \times 10^6$ cells/ml, are incubated at 37° C. for 3 hours in a culture medium containing increasing quantities of immunovector (1 to 70 $\mu$/ml). After washing and fixing, the lymphocytes are treated like the preparations of fibroblasts above for the intranuclear detection of the antibodies.

2) Test of Attachment of the Anti-DNA Antibodies to the Lymphoid Cells

To demonstrate a reaction with the cell membranes, $10^6$ mouse thymocytes or splenocytes were incubated at cold temperature for 45 minutes with 0.1 ml of different monoclonal antibodies diluted in a solution of bovine albumin at 0.1% containing 0.2% sodium azide. After washing, the cells are incubated with fluorescent anti-mouse IgG antibodies for 45 minutes at cold temperature. After washing, the cells are examined by FACS and the number of positive cells determined in each population.

Of the 20 monoclonal antibodies examined, approximately half secrete antibodies which are capable of penetrating into the nucleus of the cells whereas the other half do not have this capacity. A correlation was able to be established between the monoclonal antibodies penetrating with a high efficiency into the nucleus of the cells (number of labelled cells, limiting dilution to obtain a labelling) and their ability to label the thymocytes and the splenocytes.

II Preparation of Immunovectors Carrying Haptens, Proteins or Nucleic Acids

A) Preparation of F(ab')2 and Fab' Fragments of Immunovectors

The F(ab')2 fragments of the immunovectors are prepared according to described methods involving proteolysis with pepsin followed by reduction by cysteine to obtain the Fab' fragment (14). Thus in 5 ml of 0.1 M citrate-citric acid buffer, pH 3.5, containing 5 mg of immunovector, 150 $\mu$g of pepsin are added and the mixture is incubated for 2 hours at 37° C. The medium is adjusted to pH 8 and the preparation filtered on a protein A-Sepharose column in order to remove the undigested IgG's. After dialysis against PBS, this F(ab')2 preparation is stored at −20° C. until it is used. To obtain the Fab' fragments, cysteine is added to a final concentration of 0.02 M to the F(ab')2 preparation. After 10 minutes of incubation at 37° C., 0.04 M iodoacetamide is added and the mixture is incubated for 30 minutes. This Fab' preparation is dialysed against PBS and stored at −20° C. until it is used.

B) Immunovectors/haptens

Coupling to Biotin

2 µl of a 0.1 M solution of d-biotin-N-hydroxysuccinimide ester in dimethylformamide (1 mg of the active ester in 30 µl of dimethylformamide) are added to 0.5 ml of 0.1 M phosphate buffer, pH 7, containing 1 mg of antibody. The solution is left for 1 hour at laboratory temperature and dialysed against PBS at +4° C. overnight.

Coupling to Fluorescein

20 µl of a solution of fluorescein isothiocyanate in dimethyl sulphoxide (10 mg/ml) are added to 1 ml of a 0.1 M solution of sodium carbonate containing 1 mg of antibody. The solution is left for 3 hours at laboratory temperature and dialysed against PBS at +4° C.

C) Immunovectors/proteins

Coupling with Peroxidase

Ten milligrammes of peroxidase are dissolved in 0.2 ml of 1% glutaraldehyde in 0.1 M phosphate buffer pH 6.8. After incubation at laboratory temperature for 18 hours, the solution is filtered on a Sephadex G25 column (0.9×60 cm) equilibrated with 0.15 M NaCl to remove the excess glutaraldehyde. To this activated peroxidase solution, there is added 1 ml of a 0.15 M NaCl solution containing 5 mg of antibody and 0.2 ml of 1 M carbonate-bicarbonate buffer pH 9.5. The solution is stored at +4° C. for 24 hours and then supplemented with lysine to the final concentration of 0.1 M, and 25 then dialysed against PBS at 4° C.

D) Immunovectors/nucleic Acids

Polynucleotides

The polynucleotide used was composed of 15 nucleotides and carried a fluorescein in 5' and a free $NH_2$ group in 3'. It was prepared according to conventional methods of nucleic synthesis. This nucleotide was coupled to the immunovector via p-benzoquinone (14). 0.1 ml of ethanol containing 3 mg of p-benzoquinone is added to 0.4 ml of 0.1 M phosphate buffer pH 6 containing 1 mg of immunovector (whole molecule, F(ab')2 or Fab'). After an incubation of one hour at laboratory temperature, the preparation is filtered on a Sephadex G-25 column. The fraction containing the activated immunovector is supplemented with the polynucleotide in a ratio of one molecule of immunovector to 4 molecules of polynucleotide, and the solution is adjusted to pH 9.2 with carbonate-bicarbonate buffer. After 18 hours incubation at laboratory temperature, the reaction is stopped by addition of lysine to the final concentration of 0.1 M, followed by dialysis against PBS. This preparation is stored at +4° C. until it is used.

Plasmids

Two plasmids were tested, a first carrying the vimentin promoter upstream of the gene encoding the SV40 T, t antigens (pHuVim 830 T,t) (21) and a second carrying the luciferase gene (22) under the control of a cytomegalovirus promoter (pCMV-Luc) (5).

These plasmids are maintained in the E. coli strain and are prepared after a bacterial culture by the standard lysis method in the presence of detergent and in alkaline medium. The plasmids are then purified by chromatography on a resin column (Qiagen Plasmid Kits).

The immunovectors J-20.8 and F-14.6 are used for this work. These antibodies are prepared by the method of preparation of monoclonal immunovectors previously described in paragraph I.B/. The antibodies are coupled to poly-L-lysine with the aid of a coupling agent, especially a carbodiimide, such as EDC (1-(3-dimethylaminopropyl)-1'-ethylcarbodiimide). In some cases, polyclonal IgG's are added to the anti-DNA antibody in a 10:1 ratio so as to increase the concentration of IgG in the medium and thereby to promote the coupling with the polylysine.

2 mg of monoclonal antibody (J-20.8 or F-14.6) in 1 ml of PBS or of concentrated polyclonal IgG's at 20 mg/ml are dialysed overnight against a 10 mM MES buffer, pH 5. Two mg of poly-L-lysine (MW=18,000) are dissolved in 1 ml of this same buffer and then supplemented with 0.2 mg of EDC (in 50 µl of MES buffer) for 30 seconds. The poly-L-lysine solution is then added to the antibody/EDC mixture and the incubation is continued for 2 hours.

the preparation is then filtered on a protein A-Sepharose column in order to separate the excess poly-L-lysine from the antibodies conjugated to the polylysine which are eluted at pH 3 under the usual conditions, neutralized and dialysed against PBS.

III. Examples of Transfer of Substances into the Nuclei of Cells by Immunovectors Associated with These Substances A) Transfer in vitro of Fluorescein Fibroblasts of the GM A-32 line in culture on glass coverslips are incubated at 37° C. for 2 to 4 hours in RPMI culture medium containing increasing quantities of monoclonal immunovectors (J-20.8 antibody or Fab'2 fragments) labelled with fluorescein. At the end of this time, the cells are washed and fixed as described in IC1. After inclusion in Mowiol medium, they are examined under a fluorescence microscope. Practically all the nuclei of the fibroblasts show a fluorescent labelling. On the other hand, the nuclei of fibroblasts incubated with a control monoclonal antibody Ig 2a without anti-DNA activity, which does not penetrate to the nuclei, do not exhibit any fluorescence (FIGS. 1 and 2).

B) Transfer in vivo of Fluorescein into Mouse Peripheral Lymphocytes

One mg of immunovector (monoclonal antibody C-2.1 or F-4.1 or control antibody (monoclonal antibody G-14) labelled with fluorescein is injected into two mice in an amount of 0.2 ml intraveneously and 0.3 ml intraperitoneally. After 5 hours, the mice are bled and sacrificed and the circulating blood lymphocytes are analysed by FACS. It is noted that 60% of the peripheral blood lymphocytes obtained from the mouse injected with the immunovector are fluorescent whereas none of the lymphocytes from the control animal are (FIG. 3). Microscopic examination shows a fluorescence at the level of the nuclei in the majority of the cells.

C) Transfer of Biotin

Fibroblasts of the PtK2 line ($10^5$/ml) cultured for 24 hours beforehand are incubated in a complete RPMI culture medium with human anti-DNA polyclonal IgG's labelled with biotin in increasing quantities (5–100 µg). After 3 hours, the cells are washed, fixed and permeabilized as described in IC. The cells are then incubated with RPMI containing 1 µg/ml of peroxidase-labelled streptavidin. After one hour, the cells are washed three times with PBS and the peroxidase associated with the cells is revealed using the DAB+$H_2O_2$ medium. The preparations are included in Mowiol and examined under an optical microscope. A large number of nuclei of the fibroblasts incubated with anti-DNA IgG are positive whereas the cells incubated with IgG's obtained from normal individuals and labelled with biotin are negative.

D) Transfer of Peroxidase

Under the conditions defined in paragraph IIIC, the PtK2 fibroblasts are incubated with increasing quantities of Fab' fragments of an immunovector (antibody J-20.8) labelled with peroxidase. After 3 hours, the cells are washed three times with PBS and fixed for 20 minutes with 0.2% glutaraldehyde and 2% formaldehyde in PBS. After washing, the peroxidase activity is revealed by the coloured $DAB+H_2O_2$ test and the preparations are examined under an optical microscope. A large proportion of nuclei of the fibroblasts incubated with the Fab' fragments of the J-20.8 antibody are positive for peroxidase, whereas those incubated with the control antibody 48.9 are negative.

E) Transfer of Polynucleotide Labelled with Fluorescein $3 \times 10^6$ splenocytes, prepared from BALB/c mouse spleen, are incubated in 1 ml of RPMI containing 40 µg/ml of immunovector (J-20.8) or of its Fab' fragment covalently coupled to the polynucleotide. After three hours of incubation at 37° C., the cells are washed with PBS, fixed in 4% paraformaldehyde and examined under a microscope. Eight to 10% of the cells show an intranuclear fluorescence (FIG. 4).

F) Transfer of Plasmid

The transfection efficiency was evaluated by demonstrating the synthesis of the proteins encoded by these genes, either with the aid of anti-T antigen antibodies coupled to peroxidase, or by a luminometric assay of the activity of luciferase on its substrate, luciferin.

The cells used are fibroblasts of the GMA-32 line and Hep 2 carcinoma cells. They are cultured in a complete medium (RPMI 1640 medium containing 10% foetal calf serum, 2 mM L-glutamine, 1% sodium pyruvate and antibiotics), at 37° C. of 5% $CO_2$.

Plasmid pHuVim 830 T,t: The Hep2 cells are inoculated the day before in an amount of $2 \times 10^4$ cells in 0.5 ml of complete medium per well of a 24-well plate. For the transfection, the medium is removed and replaced with 0.3 ml of complete medium containing 20 µg of antibody-poly-L-lysine and 2 µg of plasmid, or 20 µg of native antibodies and 2 µg of plasmid or 2 µg of plasmid alone. After 6 hours, the medium is changed and the culture is continued by changing the medium every two days and by subdividing the cells into two if necessary. The transfection efficiency is tested at variable times.

Plasmid pCMV-Luc: The GMA-32 cells are inoculated the day before in an amount of 7 to $10 \times 10^4$ cells/0.5 ml of complete medium per well of a 24-well plate of complete culture medium. For the transfection, the medium is removed and replaced with 0.5 ml of complete medium containing 8 µg of J-20.8/polylysine or of F-14.6/polylysine, or 20 µg of J-20.8 polyclonal IgG and 2 µg of plasmid or 2 µg of plasmid alone. After 6 hours, the medium is changed. The transfection efficiency is tested 24 hours after the start of transfection.

Control of Transfection

Plasmid pHuVim 830 T, t: The synthesis of the T antigen in the nucleus of the transfected cells is demonstrated by an immunocytochemical method. The cells are washed 3 times with PBS and then fixed for 10 minutes in methanol at −20° C. They are then incubated with the anti-T antigen antibody coupled to peroxidase for 1 hour. After washing, the peroxidase is revealed with the $DAB+H_2O_2$ mixture. In the well incubated with the J-20.8 polylysine and plasmid complex, isolated cells and a few clusters of cells have a nucleus which is intensely coloured brown after 48 hours and after 2 weeks. The control with the native antibody or the plasmid alone is negative.

Plasmid pCMV-Luc: The transfection efficiency is demonstrated by the luciferase synthesis detectable in the lysates of the transfected cells. This enzyme catalyses the oxidation of luciferin which results in a product detectable in a luminometre. After the culture, the cells are washed in PBS and then lysed in 25 mM tris-phosphate buffer, pH 7.8, containing 8 mM $MgCl_2$, 1 mM DTT, 1% triton X100, 1% BSA and 15% glycerol. The lysate is assayed in a luminometre by automated addition of a solution of luciferin (0.25 mM) and of ATP (1 mM). An aliquot of the same lysate is assayed for its protein concentration using a Coomassie (Bio-Rad Protein Assay) reagent. The results are expressed in units (RLU) per mg of proteins. As shown in the table, a gene transfer takes place in the presence of the antibody preparations J-20.8/polylysine and F-14.6/polylysine whereas the IgG/polylysine preparations have no effect.

The transfection efficiency for the same antibody/plasmid ratio is 10 times higher with the J-20.8 preparation than with F-14.6. Furthermore, the addition of concentrated polyclonal IgG's during the coupling to polylysine appears to increase the transfection efficiency since 2 µg of J-20.8 (complex 20:0.5) of the J-20.8-IgG/polylysine preparation give results of the same order of magnitude as 8 µg (complex 8:0.5) of the J-20.8/polylysine preparation.

The entire results obtained are summarized in the following table:

| Immunovector | Antibody/plasmid ratio µg/µg | Assay RLU/mg × $10^4$ |
|---|---|---|
| J-20.8-IgG/polylysine | 20:0.5 | 5.8 |
|  | 20:0.5 | 63.00 |
| J-20.8/polylysine | 8:2 | 2.00 |
|  | 8:1 | 15.00 |
|  | 8:1 | 38.00 |
|  | 8:0.5 | 13.00 |
| F-14.6/polylysine | 8:0.5 | 1.3 |
| IgG/polylysine | 20:0.5 | <0.1 |
|  | 20:0.5 | <0.1 |
| Plasmid alone (µg) | 2 | <0.1 |
|  | 1 | <0.1 |
|  | 0.5 | <0.1 |

In the preceding text, the preferred immunovectors consisted essentially of the anti-DNA antibodies or of fragments of these antibodies, with the proviso that these fragments retain the site of recognition for the whole DNA. Naturally, it goes without saying that the immunovectors which can be used within the framework of the invention may be prepared in any other way, as long as they would also allow the transport of the biologically active principle which would be associated therewith through the membranes of these cells and their cytoplasm and its transfer close to the nucleus of the cells, or even inside this nucleus.

By way of examples of such immunovectors, there may be mentioned conjugates between a nuclear protein, for example a histone, a protein hnRNP, a polymerase or a factor associated with this polymerase, and the active product, this nuclear protein being itself (unless it is capable, on its own, of bringing about the internalization and the transfer of a biologically active principle into the nucleus of the cells, conjugated to the anti-cell membrane receptor antibody or to any other molecule allowing the internalization into the cell of the conjugate thus produced. As long as this conjugate is capable of diffusing as far as the nucleus of the cells and that, moreover, it may in turn transport and transfer, as was defined above, a biologically active principle which would be coupled to this conjugate, it constitutes an immunovector entering within the framework of the present invention.

The selection techniques which have been described above for the choice of efficient immunovectors for the transfer of an active principle to the nucleus of the cells are equally applicable to the selection of the abovementioned conjugates.

Persons skilled in the art will understand that an additional criterion for choice may, at least for some of the conjugates used, lie in the absence of an undesirable action of the nuclear protein which it contains with the cell function. It is in fact to be noted that only the part of the intranuclear protein carrying its site of recognition of the corresponding DNA is essential for the embodiment in accordance with the invention.

LEGEND TO THE FIGURES

FIG. 1: Transfer of fluorescein "in vitro"

Labelling of the nuclei of the GMA 32 fibroblasts with an immunovector labelled with fluorescein (antibody J-20.8) in A and B (×100 magnification).

C: Absence of labelling with the fluorescent control antibody (×100).

D: Another field observed at low magnification (×40).

Figure 2A:
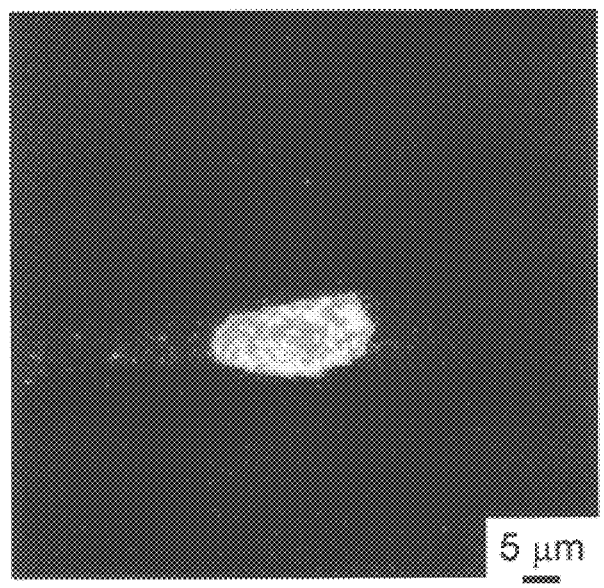
Figure 2B:
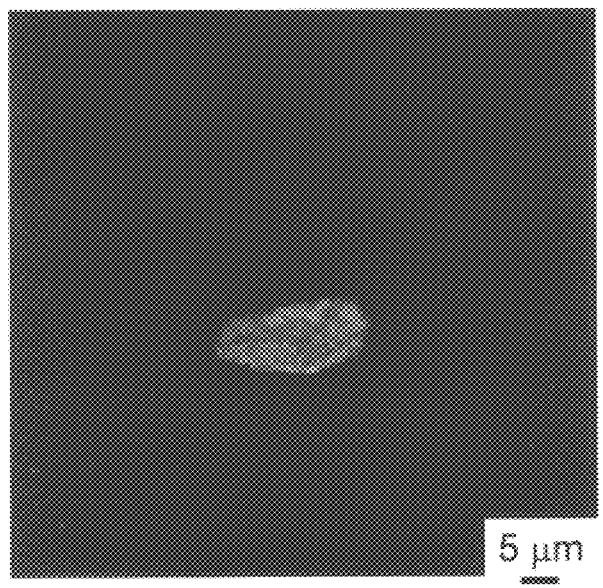

FIG. 2: Same preparation as that of FIG. 1A analysed under a confocal microscope. The GMA 32 fibroblasts are labelled essentially in the nucleus. A total fluorescence may be noted in FIG. 2A. FIG. 2B corresponds to the analysis of the fluorescence intensity.

Figure 3B:
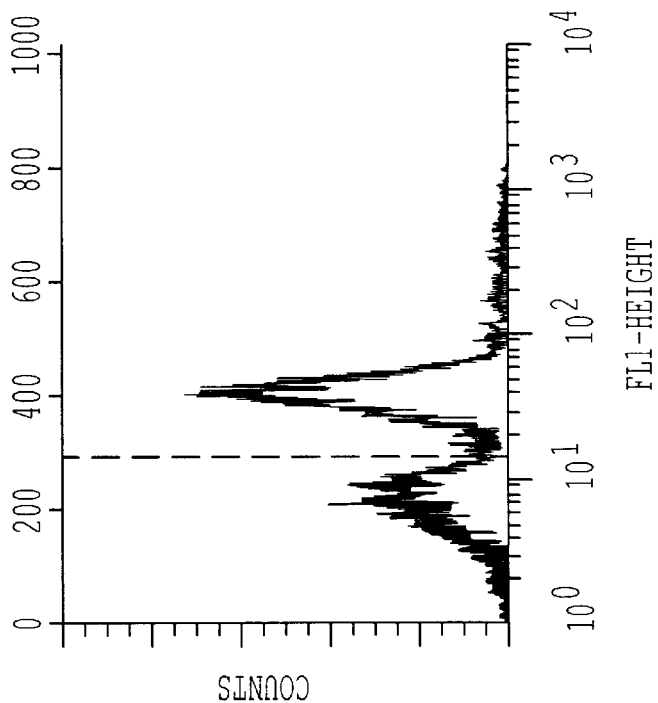
Figure 3A:
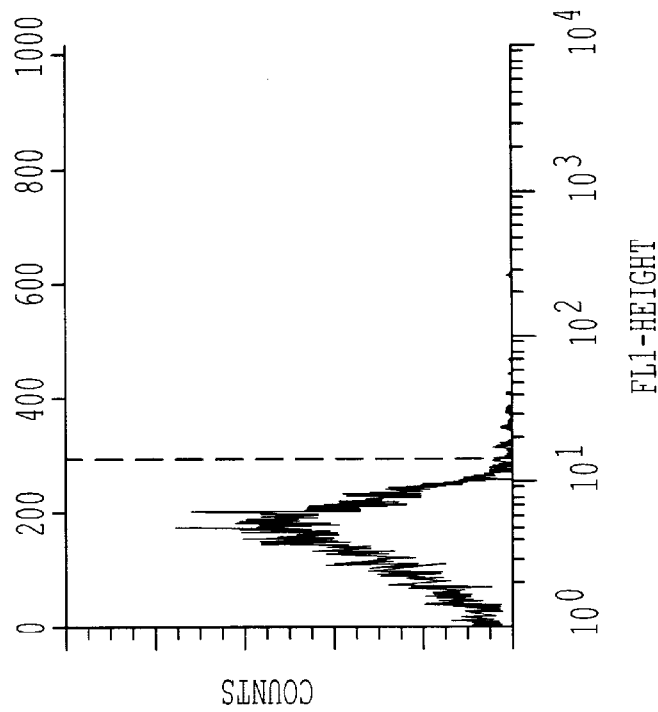

FIG. 3: Transfer of fluorescein "in vivo" FACS analysis of mouse peripheral blood cells injected 5 hours beforehand in FIG. 3A, the fluorescent control antibody and in FIG. 3B with a fluorescent immunovector the antibody (J-20.8). Histogrammes representing on the x-axis the fluoresence intensity (in arbitrary units) and on the y-axis the number of cells.

Figure 4A:
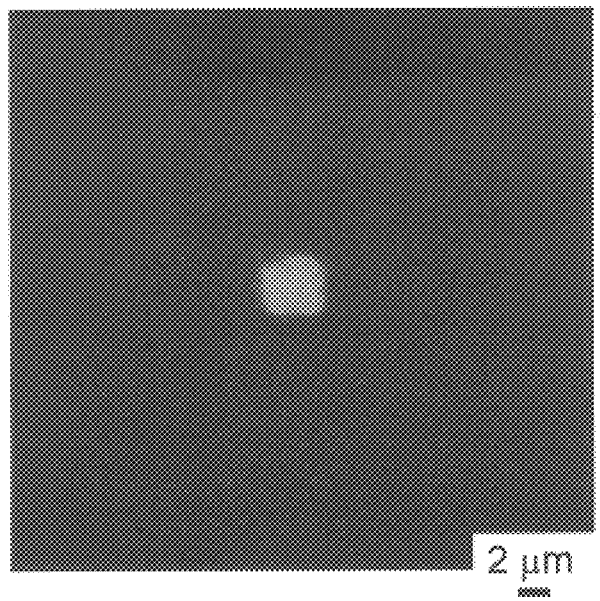
Figure 4B:
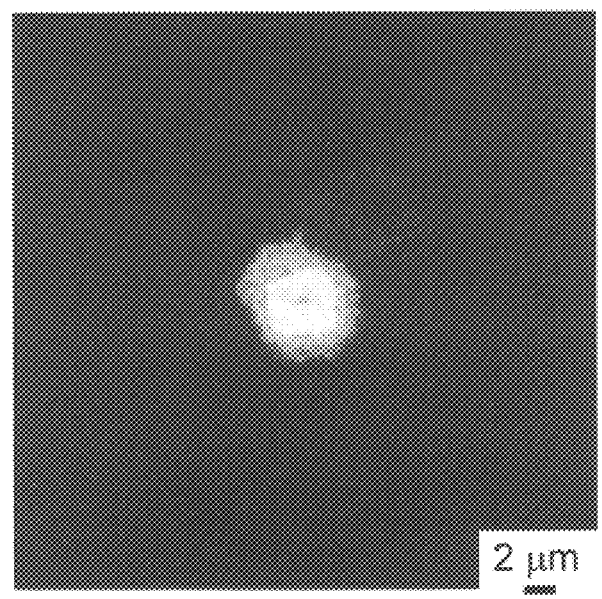

FIG. 4: Analysis of the peripheral blood cells (of FIG. 3) by confocal microscopy. A total fluorescence can be noted in FIG. 4A. FIG. 4B corresponds to analysis of the fluorescence intensity.

Figure 5A:
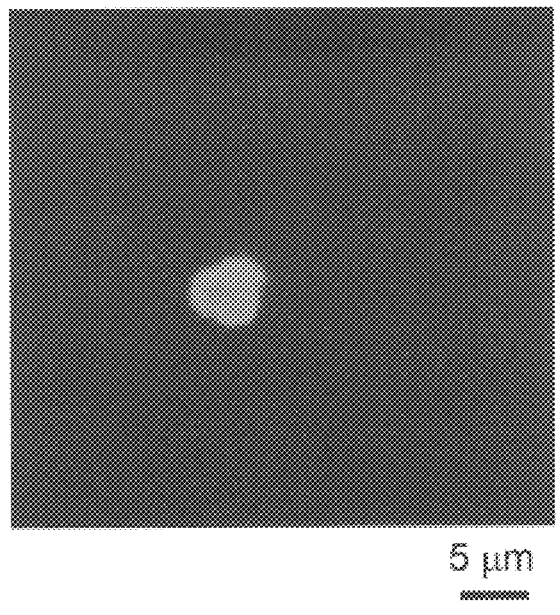
Figure 5B:
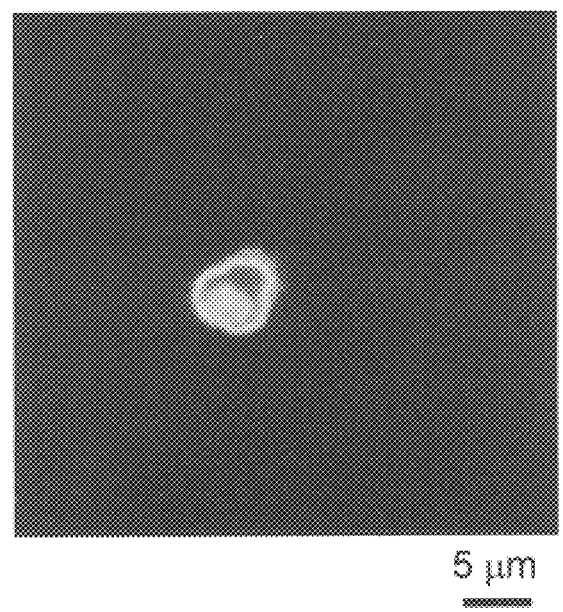

FIG. 5: Transfer of a nucleotide "in vitro" Confocal microscopy examination of a mouse splenocyte into which has penetrated the Fab' fragment of an immunovector (antibody J-20.8) coupled to a fluorescent nucleotide. A total fluorescence is observed in FIG. 5A. FIG. 5B corresponds to analysis of the fluorescence intensity.

REFERENCES (1) "Non-viral therapy", Current Opinion on Biotechnology, Vol. 5, pp. 626–636, (1994), Ledley F. D.

(2) T. D. McKee, M. E. DeRome, G. Y. W U and M. A. Findeis. Preparation of asioloorosolucoid-polylysine conjugates. Bioconjugate Chem., 5:306 (1994)

(3) Receptor-mediated endocytosis and nuclear transport of transfecting DNA construct. A. A. Rosenkrank, S. V. Yachmenev, D. A. Jans, N. V. Serebryakova, V. I. Murav'ev, R. Peters and A. S. Sobolev. Exp. Cell Res., 199:323 (1992).

(4) Receptor-mediated endocytosis of transferrin-polycation conjugates: an efficient way to introduce DNA into hematopoietic cell. M. Zenke, P. Steinlein, E. Wagner, M. Cotte, H. Beug, and M. L. Birnstiel. Proc. Natl. Acad. Sci. USA, 87:3655 (1990)

(5) J. R. Merwin, E. P. Carmichael, G. S. Noell, M. E. DeRome, W. L. Thomas, N. Robert, G. Spitalny and H. C. Chiou. CD5-mediated specific delivery of DNA to T lyphocytes: compartmentalization augmented by adenovirus. J. Immunol. Methods, 186:257 (1995).

(6) E. Wagner, K. Zatloukal, M. Cotten, H. Kirlappos, K. Mechtler, D. T. Curiel and M. L. Birnstiel. Coupling of adenovirus to transferrin-polylysine/DNA complexes enhances receptor-mediated gene delivery and expression of transfected genes. Proc. Natl. Acad. Sci. USA 89:6099 (1992).

(7) "Antibody to nuclear ribonucleoprotein penetrates live human mononuclear cells through Fc receptors", Nature, Vol. 271 (1978), Donarto Alarcon-Segovia et al.

(8) "Antibody penetration into living cells", The Journal of Immunology, Vol. 122, (1979), Donarto Alarcon-Segovia et al.

(9) "$V_H$ gene analysis of spontaneously activated B cells in adult MRL-lpr/lpr mice", The Journal of Immunology, Vol. 147, pages 1504–1511, (1991), Mary H. Foster et al.

(10) "Murine Monoclonal Anti-DBA Antibodies Penetrate Cells, Bind to Nuclei and Induce Glomerular Proliferation and Proteinuria In Vivo", J. Am. Soc. Nephrol., Vol. 2, pp. 1345–1354 (1992), Demetrios Vlahakos et al.

(11) "Monoclonal Murine anti-DNA antibody interacts with living mononuclear cells", Arthritis and Rheumatism, Vol. 30 No. 6, pp. 669–678, (1987), Okudaira et al.

(12) "Cross-reactions of anti-DNA autoantibodies with cell surface proteins", Eur. J. Immunol. Vol. 23, pp. 383–390, (1993), Eyal Raz et al.

(13) "Life Science & Analytical Research Products"; Pierce Interchim

(14) "Techniques immunoenzymatiques" [Immunoenzymatic techniques], Editions Inserm, (1987), Ternynck T. and Avrameas S.

(15) "DNA affinity column chromatography: application in the isolation of distinct antibody populations SLE sera., Clin. Exp. Immunol. Vol. 62, pp. 321–328, (1985) Kubota et al.

(16) "An antibody chimera technique applied to enzyme immunoassay for human alpha-1-fetoprotein with monoclonal and polyclonal antibodies", J. Immunol. Methods, (1984) Vol. 66, pp. 179–185, Porstmann B. et al.

(17) "Development of a bispecific monoclonal antibody for use in molecular hybridization, J. Immunol. Methods, (1994), Vol. 169, pp. 123–133, Auriol J. et al.

(18) "Targeted replacement of the homeobox gene Hox-3.1 by the *Escherichia coli* lacZ in mouse chimeric embryos", Genetics, Proc. Natl. Acad. Sci. USA, (1990), Vol. 87, pp. 4712–4716, Le Mouellic et al.

(19) "DNA-mediated immunization and the energetic immune response to hepatitis B surface antigen", Clin. Immunology and Immunopathology, (1995), Vol. 75, pp. 1–12, Whalen R. G. et al.

(20) "Rehasping human antibodies for therapy", Nature, (1988), Vol. 332, pp. 323–327, Riechmann et al.

(21) "B. Schwartz, P. Vicart, C. Delouis and D. Paulin, Mammalian cell lines can be efficiently established in vitro upon expression of the SV40 large T antigen driven by a promoter sequence derived from the human vimentin gene. Biol. Cell., 72:7 (1991).

(22) S. K. Nordeen. Luciferase reporter gene vectors for analysis of promoters and enhancers. Bio Techniques, 6:454 (1988).

What is claimed is:

1. A product comprising an antibody which recognizes an epitope contained in a nucleic acid, said antibody is coupled to a biologically active principle, wherein said biologically active principle is a protein, or a nucleic acid; and wherein said antibody is produced by a hybridoma selected from the group consisting of I-1605, I-1606, and I-1607.

2. The product of claim 1, wherein said nucleic acid is an antisense oligonucleotide.

3. The product of claim 1, wherein said nucleic acid is a recombinant plasmid.

4. The product of claim 1, wherein said protein is an enzyme, an enzyme inhibitor, or an enzyme activator.

5. The product of claim 1, further comprising polylysine.

6. A method of preparing the product of claim 1, comprising coupling the antibody with said biologically active principle.

7. The method of claim 6, wherein said coupling is non-covalent.

8. The method of claim 6, wherein said coupling is covalent.

9. The method of claim 6, wherein said coupling is mediated by a chemical coupling agent.

10. The method of claim 9, wherein said chemical coupling agent is selected from the group consisting of gluteraldehyde, imido esters, N-hydroxysuccinimidyl esters, maleimides, azidobenzoyl hydrazide, carbodiimide, and benzoquinone.

11. The method of claim 10, wherein said carbodiimide is EDC (1-(3-dimethlyaminopropyl)-1'-ethylcarbodiimide).

12. A method of transferring a biologically active principle of interest into a cell comprising:

coupling an antibody which recognizes an epitope contained in a nucleic acid with the biologically active principle thereby forming a coupled biologically active principle; and incubating the coupled biologically active principle with the cell, wherein said coupled principle is transferred through the cell membrane and into the cell and wherein said biologically active principle is a protein, or a nucleic acid.

13. The method of claim 12, wherein said nucleic acid is an antisense oligonucleotide.

14. The method of claim 12, wherein said nucleic acid is a recombinant plasmid.

15. The method of claim 12, wherein said protein is an enzyme, an enzyme inhibitor, or an enzyme activator.

16. The method of claim 12, wherein said coupled biologically active principle is further coupled to polylysine.

17. The method of claim 12, wherein said antibody is produced by a hybridoma selected from the group consisting of I-1605, I-1606, and I-1607.

* * * * *